US00PP36434P2

(12) United States Plant Patent
Smith

(10) Patent No.: US PP36,434 P2
(45) Date of Patent: Feb. 11, 2025

(54) ***BUXUS* PLANT NAMED 'WINTER JADE'**

(50) Latin Name: *Buxus microphylla*
Varietal Denomination: WINTER JADE

(71) Applicant: Michael Smith, Parsons, TN (US)

(72) Inventor: Michael Smith, Parsons, TN (US)

( * ) Notice: Subject to any disclaimer, the term of this patent is extended or adjusted under 35 U.S.C. 154(b) by 0 days.

(21) Appl. No.: 18/809,669

(22) Filed: Aug. 20, 2024

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Cassandra Bright

(57) ABSTRACT

A new and distinct cultivar of *Buxus* plant named 'WINTER JADE' is disclosed, characterized by an upright plant habit with dense branching and dense foliage cover. Plants have shown resistance to the normal diseases and pests of Boxwood. Foliage is dark lush green. Plants have been observed to tolerate temperatures between 0 degrees F. to 110 degrees F. without negative effects. The dark green foliage color is maintained in both winter and summer under both low and high temperatures. The new cultivar is a *Buxus*, suitable for ornamental garden purposes.

2 Drawing Sheets

Figure 1:
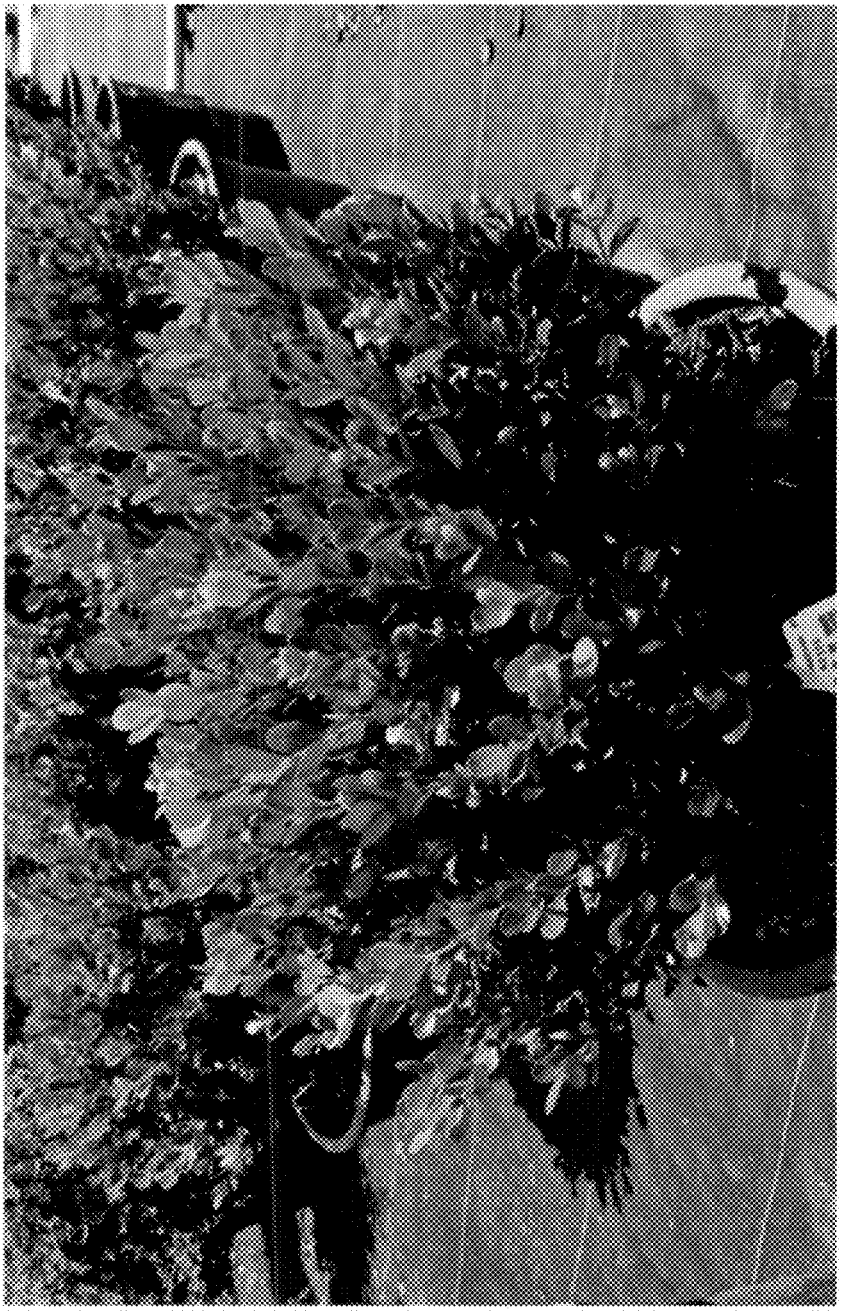

Latin name of the genus and species: *Buxus microphylla.*
Cultivar denomination: 'WINTER JADE'.

BACKGROUND OF THE INVENTION

The new cultivar, hereinafter referred to as 'WINTER JADE', was discovered at a nursery in Parsons, TN. The interesting new cultivar was discovered as a naturally occurring whole plant mutation growing in a planting of the parent variety, the unpatented *Buxus microphylla* 'Winter Gem' in May of 2019.

After identifying the new cultivar as a potentially interesting selection, the inventor first organized asexual propagation of 'WINTER JADE' in July of 2019, using semi-softwood cuttings at the same nursery in Parsons, TN. The inventor continued controlled testing and propagation, assessing stability of the unique characteristics of this cultivar. At least three generations have been reproduced and have shown that the unique features of this cultivar are stable and reproduced true to type.

SUMMARY OF THE INVENTION

The cultivar 'WINTER JADE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WINTER JADE'. These characteristics in combination distinguish 'WINTER JADE' as a new and distinct *Buxus* cultivar:

1. Upright growth habit.
2. Lush, dark green foliage.
3. Disease resistance.

4. Maintains green color in winter.
5. Cold hardy to 0 degrees F.

COMPARISON TO PARENT CULTIVAR

'WINTER JADE' is similar in most horticultural characteristics to the parent variety. Plants of the new cultivar 'WINTER JADE' however, differ in the following:

1. The new cultivar has a more upright growth habit than the parent variety.
2. Stems of the new cultivar are softer and more flexible than stems of the parent variety.
3. Plants of the new cultivar are more densely branched than plants of the parent variety.
4. The new cultivar tolerates colder temperatures than the parent variety.
5. The new cultivar grows faster and is ready for sales sooner than the parent variety.

COMMERCIAL COMPARISON

'WINTER JADE' is similar in most horticultural characteristics to the unpatented commercial cultivar *Buxus* 'Winter Green'. Plants of the new cultivar 'WINTER JADE' however, differ in the following:

1. Foliage of the new cultivar is darker green than foliage of 'Winter Green'.
2. Plants of the new cultivar are faster growing than plants of this comparator.
3. Plants of the new cultivar are more compact than plants of this comparator.
4. The new cultivar shows improved resistance to diseases compared to 'Winter Green'.

'WINTER JADE' is similar in most horticultural characteristics to the unnamed and unpatented commercial variety *Buxus microphylla* var. *japonica*. Plants of the new cultivar 'WINTER JADE' however, differ in the following:

1. Foliage of the new cultivar stays green in the winter; foliage of this comparator turns brown in the winter.
2. Plant shape of the new cultivar is upright ovate; plant shape of this comparator is round.
3. Plants of the new cultivar are denser and more compact than plants of this comparator.
4. Stems of the new cultivar are stronger and more abundant than stems of this comparator.

'WINTER JADE' is similar in most horticultural characteristics to the commercial cultivar *Buxus* 'Winter Rocket', U.S. Plant patent application Ser. No. 18/762,289. Plants of the new cultivar 'WINTER JADE' however, differ in the following:

1. Foliage of the new cultivar is about 50% narrower, having an ovate shape, compared to the very broad elliptic to globose shape foliage shape of 'Winter Rocket'.
2. Plants of 'Winter Jade' are denser, producing more branches and having shorter internodes than 'Winter Rocket'.
3. Plants of the new cultivar are more compact than plants of this comparator.
4. The new cultivar shows improved resistance to diseases compared to 'Winter Rocket'.

BRIEF DESCRIPTION OF THE PHOTOGRAPHS

The accompanying photograph in FIG. 1 illustrates in full color a typical plant of 'WINTER JADE' grown outdoors in Cairo, GA. The plant is approximately 3 years old.

Figure 2:
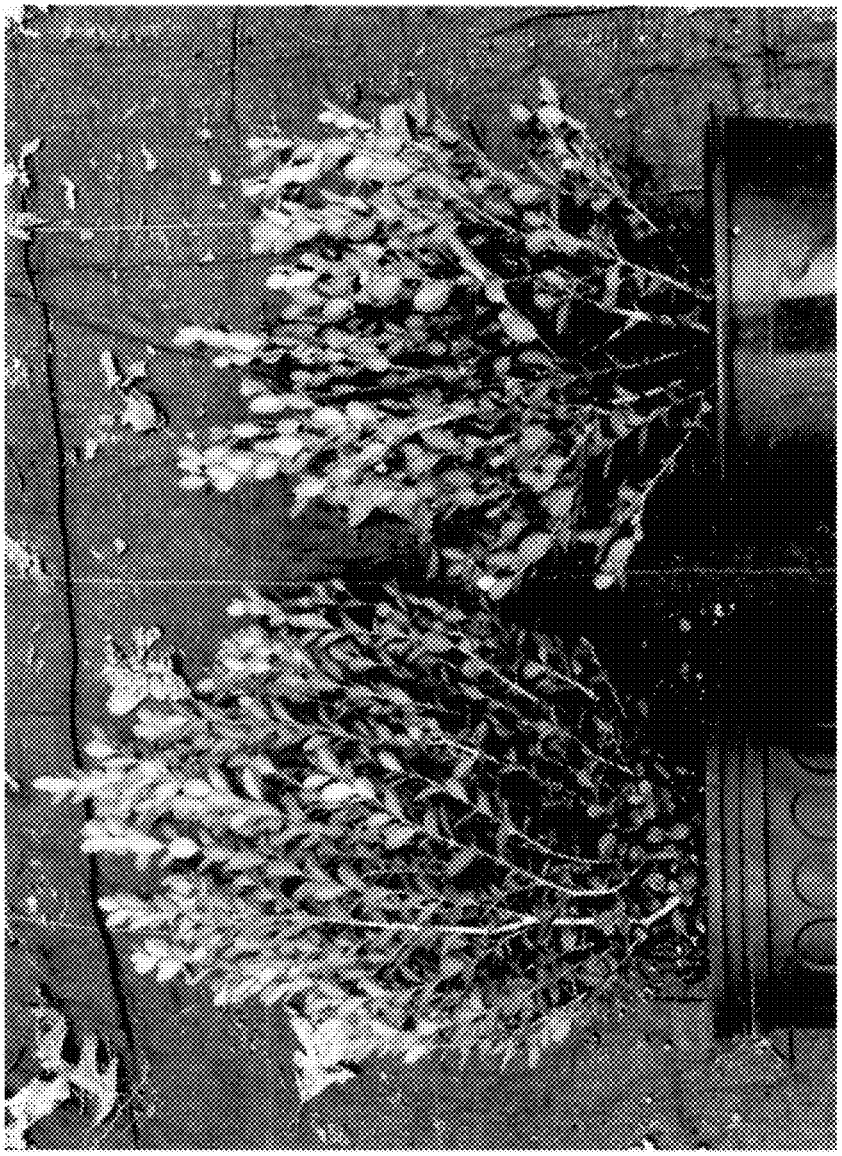

FIG. 2. is a side-view comparison with the parent variety, illustrating the more acute branching angle of the new cultivar. 'WINTER JADE' is the plant on the left of the figure, 'Winter Gem' is on the right. Plants were grown together and are both approximately 1.5 years old and unpruned.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'WINTER JADE' plants grown outdoors in Cairo, GA Plants are approximately 2 years old, in a 1-gallon nursery container. Measurements and numerical values represent averages of typical plant types.

Botanical classification: *Buxus microphylla* 'WINTER JADE'.

PROPAGATION

Time to rooting: 30 days in summer, 45 days in winter at 18° C. to 27° C.

Root description: Moderately dense, moderately free branching, non-fleshy, fine. Colored near Greyed-Orange 164D.

PLANT

Growth habit: Upright and dense.
Plant shape: Upright ovate.
Height: 28 cm.
Plant spread: 15 cm.
Growth rate: Moderate to rapid.
Branching characteristics: Basal; a single pinch near the base encourages abundant branching.
Quantity of branches: 5 to 7 main branches emerging from a basal pinch. Lateral branches occurring 4 cm to 5 cm along main branches.
Main branch internode length: 2.0 cm to 3.0 cm
Length of main branches: 19 to 34 cm.
Diameter of main branches: 4 mm.
Length of lateral branches: 7 to 22 cm.
Diameter of lateral branches: 3 mm.
Branch descriptors, main and lateral branches:
- *Shape*.—Rounded.
- *Aspect*.—Straight.
- *Angle*.—15° to from center of plant.
- *Color*.—Immature: RHS Yellow-Green 145A. Mature: RHS Grey-Brown 199C with scales Greyed-Green 197C.
- *Strength*.—Strong and flexible.
- *Texture*.—Immature: glabrous; Mature: scaly.

FOLIAGE

Leaf:
- *Arrangement*.—Opposite, single.
- *Shape of blade*.—Ovate.
- *Length*.—Average 2.4 cm.
- *Width*.—Average 1.1 cm.
- *Apex*.—Emarginate.
- *Base*.—Tapered.
- *Attachment*.—Petiolate.
- *Margin*.—Entire.
- *Texture of top surface*.—Glabrous with a slightly waxy cuticle.
- *Texture of bottom surface*.—Glabrous.
- *Appearance of top surface*.—Shiny.
- *Appearance of bottom surface*.—Matte.
- *Color*.—Young foliage upper side: RHS Yellow-Green 144C, deep flush at apex 143B. Young foliage under side: RHS Yellow-Green 145A. Mature foliage upper side: RHS Green 135A. Mature foliage under side: RHS Green 143C.
- *Venation*.—Type: Pinnate. Venation Color: Upper: Center vein Yellow-Green 145C. Lateral veins faintly visible, 145D. Lower: Center vein Yellow-Green 145C. Lateral veins faintly visible, 145D.

Petiole:
- *Length*.—Average 3 mm.
- *Diameter*.—2 mm.
- *Texture, upper side*.—Glabrous.
- *Texture, under side*.—Glabrous.
- *Color, upper side*.—RHS Green 143C.
- *Color, under side*.—RHS Green 143D.

FLOWER

Not observed to date.

REPRODUCTIVE ORGANS

Not observed to date.

OTHER CHARACTERISTICS

Fruit and seeds: Not observed.

Disease and pest resistance: Resistance to *Calonectria pseudonaviculata* has been observed. Resistance to pests of *Buxus* also observed.

High temperature tolerance: Observed to tolerate temperatures between 0° F. to 110° F. without negative effects.

Drought tolerance: No observed tolerance for drought.

What is claimed is:

1. A new and distinct cultivar of *Buxus* plant named 'WINTER JADE' as herein illustrated and described.

* * * * *